(12) United States Patent
Buydts et al.

(10) Patent No.: US 9,775,813 B2
(45) Date of Patent: Oct. 3, 2017

(54) SEPARABLE CAPSULE

(71) Applicant: Capsugel Belgium NV, Bornem (BE)

(72) Inventors: Hilde Buydts, Helenalei (BE); Stefaan Jaak Vanquickenborne, Rijmenam (BE)

(73) Assignee: Capsugel Belgium NV, Bornem (BE)

( * ) Notice: Subject to any disclaimer, the term of this patent is extended or adjusted under 35 U.S.C. 154(b) by 0 days.

(21) Appl. No.: 14/774,119

(22) PCT Filed: Feb. 13, 2014

(86) PCT No.: PCT/IB2014/058948
§ 371 (c)(1),
(2) Date: Sep. 9, 2015

(87) PCT Pub. No.: WO2014/181200
PCT Pub. Date: Nov. 13, 2014

(65) Prior Publication Data
US 2016/0022593 A1    Jan. 28, 2016

Related U.S. Application Data (60) Provisional application No. 61/821,753, filed on May 10, 2013.

(51) Int. Cl.
*A61K 9/48* (2006.01)
*A61J 3/07* (2006.01)

(52) U.S. Cl.
CPC ............. *A61K 9/4808* (2013.01); *A61J 3/071* (2013.01); *A61J 3/072* (2013.01); *A61J 2205/30* (2013.01)

(58) Field of Classification Search
USPC .......................................................... 424/454
See application file for complete search history.

(56) References Cited

U.S. PATENT DOCUMENTS

| | | |
|---|---|---|
| 3,399,803 A | 9/1968 | Oglevee et al. |
| 3,823,843 A | 7/1974 | Stephens et al. |
| 4,040,536 A | 8/1977 | Schwarz |
| 4,076,848 A | 2/1978 | de Limur |
| 4,792,451 A | 12/1988 | Kim |
| 5,587,177 A | 12/1996 | Grimberg |
| 5,769,267 A | 6/1998 | Duynslager et al. |

FOREIGN PATENT DOCUMENTS

| | | |
|---|---|---|
| CA | 2900305 | 11/2014 |
| EP | 2994114 | 3/2016 |
| GB | 2172569 | 9/1986 |
| JP | 2016522713 | 8/2016 |

OTHER PUBLICATIONS

International Search Report and Written Opinion for PCT/IB2014/058948 (mailed Jun. 10, 2014).
International Preliminary Report on Patentability for PCT-IB2014-058948 (mailed Nov. 10, 2015).
Stegemann, S., et al., "Swallowing dysfunction and dysphagia is an unrecognized challenge for oral drug therapy," *Int J Pharm.*, 430(1-2):197-206 (Jul. 2012).

*Primary Examiner* — Devang Thakor
(74) *Attorney, Agent, or Firm* — Klarquist Sparkman, LLP (57) ABSTRACT

The present disclosure relates to a separable hard capsule for containing a medication. The capsule may be opened by finger force and used, for example, by pediatric and geriatric patients.

20 Claims, 5 Drawing Sheets

SEPARABLE CAPSULE

This is the U.S. National Stage of International Application No. PCT/IB2014/058948, filed Feb. 13, 2014, which was published in England under PCT Article 21(2), which in turn claims the benefit of U.S. Provisional Patent Application No. 61/821,753, filed on May 10, 2013, both of which are hereby incorporated in their entireties, by reference.

DESCRIPTION

The present disclosure relates to a capsule for containing a medication, and more particularly, to a reopenable hard capsule. The capsule may be opened by hand and used, for example, by pediatric and geriatric patients.

The recipient of an oral medication must be willing and able to swallow the medication for proper administering. Medication prescribed for oral ingestion is often manufactured and distributed in the form of a pill or within a capsule. Some pediatric and geriatric patients, however, may be unwilling or unable to swallow and ingest the pill or capsule. This dilemma is discussed in an article titled "Swallowing dysfunction and dysphasia is an unrecognized challenge for oral drug therapy," by S. Stegemann, M. Gosch, and J. Breitkreutz, *International Journal of Pharmaceutics*, July 2012. The article highlights that swallowing issues are an increasing problem of the aging population as they can adversely affect administration of oral medication.

An alternative to swallowing and ingesting a whole pill or capsule is taking the medication in powder or liquid form. This can include taking a medication out of a capsule, mixing the powder or liquid with food or additional liquid, and eating or drinking the mixture. Eating the medication is possible if the medication is in liquid or solid form and can be mixed with a food that is easily accepted by a patient, for example, yogurt or custard. If the medication is in liquid form or dissolvable in a liquid, for example, water or juice, the patient may drink the medication.

Medication in pill form can be difficult to dissolve in liquid or mix in food unless the pill is pulverized into smaller pieces or a powder. However, pulverizing a pill can be difficult for young or old patients, and a portion of the pill may be lost unintentionally, reducing the dose of medication.

In contrast to a solid pill, a capsule can contain medication in the form of a liquid, powder, granular material, solid, semi-solid, fibers, or combination of such forms. Rather than pulverizing a solid pill, a capsule may contain the medication in a state ready for mixing with liquid or food.

There are two main types of capsules, soft-shelled and hard-shelled. Soft-shelled capsules are primarily used for oils and active ingredients that are dissolved or suspended in oil. The soft shelled capsule is typically a single piece. Hard-shelled capsules are usually comprised of two pieces that are telescopically coupled together during manufacturing. However, standard hard capsules are not designed to be reopened once filled with the medication and fully closed after filling.

Examples of hard capsules include, for instance, a gelatin capsule such as CONI-SNAP® capsule (commercially available from CAPSUGEL®), a corn starch capsule, a hydroxypropyl methylcellulose capsule such as HPMC capsules (commercially available from CAPSUGEL®, see VCAPS® and VCAPS PLUS® capsules), and pullulan-based capsules (commercially available from CAPSUGEL®, see PLANTCAPS® capsules). Hard capsules can contain different volumes of medication depending on the length and diameter of the capsule. Capsules can come in standard and elongated sizes that include Size No. 000, No. 00 No. 0, No. 1, No. 2, No. 3, No. 4, and No. 5.

Standard medication or pharmaceutical hard capsules designed for oral ingestion, for example, telescope-type capsules, consist of two parts, a cap and a body. The cap is usually tubular or cylindrically shaped, with a closed end and open end. The body usually has a similar shape, but with a slightly smaller diameter allowing telescopic insertion into the cap.

Some cap and body pieces are designed to be reopenable for filling or processing purposes. Typically, these cap and body pieces are coupled together in a "prelock" or "preclosed" condition in which the body part is at least partially located within the cap. The cap and body remain coupled in the "prelock" condition until they are filled with medication. Before filling, the two pieces are separated. The body is filled with medication and then the two pieces are fully closed and locked together.

Maintaining a suitable prelock condition can be problematic. On the one hand, the capsule parts should readily separate in the filling machine. Thus, a low prelock force is desirable. One the other hand, the preclosed capsules must withstand transport to the filling apparatus without separation of the cap from body. This ideally requires a high prelock force. The variation of prelock force of individual capsules should be as low as possible to allow for predictable separation of pieces. A capsule having suitable prelock force and/or prelock force variation is described in commonly assigned U.S. Pat. No. 5,769,267 ("the '267 patent"), which is herein incorporated by reference in its entirety. The two-piece hard capsule described in the '267 patent has a prelock force range of 10 grams to 30 grams.

The force needed to open a two-piece hard capsule from a closed condition (including a prelocked condition) may be measured using a force gauge. Thus, a two-piece hard capsule may be placed in a closed condition and positioned in a holder. The holder secures the capsule such that one end may be rendered stationary. The cap and the body are then separated in a controlled manner, e.g., by application of steady force along the longitudinal axis of the closed capsule. The force needed to achieve the separation is then recorded. Reasonable "finger" force for a capsule designed to be reopened ranges from about 30 grams to about 200 grams, and may be from about 50 grams to about 150 grams. In some embodiments, the finger force for a capsule designed to be reopened range from about 100 grams to about 150 grams.

Similar to the prelock condition, the fully closed condition has desirable performance characteristics. For example, most medication administration involves capsules designed to remain fully closed indefinitely. However, some administration may require the capsule to be reopened, allowing the contents of the capsule to be sprinkled out and administered in combination with a food or drink. Ideally, capsules designed to be reopened should also remain fully closed in cases where the medication is to be administered in capsule form.

Current capsules configured to have prelocked and fully closed positions generally have disadvantages associated with the opening force range or the prelock force range, and sometimes both. For example, the '267 patent capsule has a suitable prelock force range (i.e., about 10-30 grams) for some uses, while exhibiting a relatively high opening force (i.e., about 400-800 grams). The high opening force may provide a reliable fully-closed condition, but the opening force required to reopen can be too high. A person may not be able to apply enough force to separate the two parts and reopen the capsule, or the applied force will break the capsule and waste the medication. Other capsule designs may have a lower opening force range that allows a person to reopen the capsule, but the opening force can be too low and therefore susceptible to accidental separation of the capsule parts. Capsules lacking specific closed position features or fixed closing or prelocked positions have variations in closed or prelocked length, which can create issues in packaging (i.e., blister packaging) and/or in printing. Additionally, current reopenable capsules configured to have prelocked and fully closed positions also have disadvantages associated with variation in the prelocked or preclosed capsule length. Since modern filling and processing methods use automated processes to open prelocked capsules, variation in capsule geometry may adversely affect the uniformity of the final product. Additionally, variation in capsule geometry may result in failure to print radially; currently available reopenable capsules may be limited in only being printable in an axial direction; upon a printing trial of rectified radial printing (#00 print pockets and #0 feed drum, engraved roll R9034, style 10×7), the capsules failed to rectify in the feed drum, the print machine failed to run and the guide wire broke. Examples of such capsules are made by Capsugel and sold by Nutra for veterinary applications; these capsules have only a single locking ring.

There are numerous patents directed towards locking hard capsules. For example, U.S. Pat. No. 3,399,803 describes a separation resistant capsule which remains intact without unintended loosening or dislodgement of the cap from the body. In addition, the cap and body enter into a fully locked position. U.S. Pat. No. 3,823,843 describes a mechanical lock position between the cap and body pieces of the capsule when the two pieces are completely telescoped together. U.S. Pat. No. 4,040,536 describes tooth-like projections to lock the body and cap against relative axial and rotational movement providing a reliable seal which is not broken when capsules are packaged, transported and subsequently treated. U.S. Pat. No. 4,792,451 describes a capsule comprising a cap and body circumferential slots for slidably locking of cap and body members during final locking.

The '267 patent disclosed above describes optimized design parameters and increased SNAP-FIT® force design creating a permanent connection. In contrast, some patents have designs directed to capsules or encapsulated products that are openable and allow for sprinkling of the material enclosed. For example, U.S. Pat. No. 4,076,848 discloses capsules for use with pulverized dehydrated fruits and vegetables that contain small amounts of the product. The capsules are designed to be easily opened and re-closed, in order to choose the desired amount of product. U.S. Pat. No. 5,587,177 discloses a capsule that is easily openable to allow for removal of the contents, but this capsule is designed not to be re-closeable.

However, none of capsules disclosed in the foregoing documents have a prelock condition and a suitable opening force range. In order to overcome the limitations of the prior art, the present disclosure describes a hard capsule with an opening force range that allows a person to reopen the capsule with finger pressure while still reliably maintaining the closed position. The capsule may also have an acceptable prelock force range, low force variation, low variability in the length of the capsule in the prelock and closed conditions, and is able to be filled, processed, and printed on high speed automated capsule machines.

Such capsules can be readily used by pediatric and geriatric patients if they have more difficulty taking medication orally in pill or capsule form. It is also understood that the capsule described by the present disclosure is not limited to use in the pediatric and geriatric fields.

SUMMARY

In accordance with an embodiment, a two-piece releasable hard capsule may include a first part having an open end, a closed end, insertion axis, and a first connection unit having a lock area comprising a plurality of first coupling elements. The two-piece releasable hard capsule may also include a second part having a second connection unit. The second connection unit may have an engagement area comprising a second coupling element, and the engagement area may be configured to engage with the lock area when the second part is fully inserted in the first part to form a connection releasable by a finger force. When the second part is fully inserted in the first part, in a fully closed position, only the connection between the first coupling elements and the second coupling element may provide a, typically mechanical, locking force holding the first and second parts together to form the connection. The locking force may be less than the finger force. The engagement area and the lock area may be arranged to engage without substantial deformation. The first coupling elements may comprise protrusions substantially elongate in shape, typically all said protrusions being elongate in shape. The elongate protrusions may comprise a restriction edge generally perpendicular to the insertion axis, this may have the further advantage of ensuring a constant average capsule length (body plus cap), particularly when a pre-lock position is used, to further improve pocket fill rate in the manufacturing process (e.g. in printing of capsules). The second coupling element may comprise an indentation having a recessed ring that may extend along the entire circumference of the second part, such may bring advantages such as easy location of first and second parts upon locking as well as reduced risk of deflections on surfaces of the first and/or second parts.

In accordance with another embodiment, a two-piece releasable hard capsule may include a first part having an open end, a closed end, insertion axis, and a first connection unit. The first connection unit may include an inner wall defining a first cavity, a prelock area, and a lock area. At least part of the lock area may be located between the prelock area and the closed end. The two-piece releasable hard capsule may also include a second part having a second connection unit. The second part may include an outer wall which is insertable into the first cavity generally along the insertion axis through the open end; and an engagement area configured to engage with the prelock area when the outer wall is partially inserted in the first cavity to form a first releasable connection between the first part and the second part. The engagement area may be configured to engage with the lock area when the outer wall is fully inserted in the first cavity to form a second releasable connection between the first part and the second part.

In a further embodiment, a two-piece releasable hard capsule may include a first part having an open end, a closed end, insertion axis, and a first connection unit. The first connection unit may include a prelock area and a lock area. The two-piece capsule may also include a second part having a second connection unit. The second connection unit may include an engagement area. The first connection unit and second connection unit may be configured to form a first releasable connection between the prelock area and the engagement area and a second releasable connection releasable by finger pressure between the lock area and the engagement area.

In any embodiment, the two-piece releasable hard capsule may be arranged such that the area of contact between the lock area and the engagement area is from 20% to 50%, preferably from 30% to 45%, of the total surface area of the engagement area (such may be the same also for the area of contact between the first and second connection units). This arrangement may bring the advantage of ensuring sufficient locking force to avoid unexpected and premature opening of the capsule (e.g. during transportation and handling) whilst at the same time, said force, still being sufficiently low for a target subject to easily open the capsule by applying pressure with one or more fingers to separate the first and second parts, when the content is to be poured out. The area of contact may be measured by dividing the sum of the surface area of the lock area (e.g. the sum of the surface area of the plurality of coupling elements) and divide by the total surface area of the engagement area.

Certain embodiments include a method of using a two-piece releasable hard capsule for administering medication. The method may include providing a two-piece releasable hard capsule at least partially filled with a medication. The method may further include applying a finger force to the two-piece releasable hard capsule to disengage a releasable connection and separate the two-pieces of the capsule. In addition, the method may include removing the medication from the two-pieces of the capsule and combining the medication with at least one of a food or a drink to produce a mixture. Finally, the method may include providing the mixture to a patient for consumption.

Additional objects and advantages of the present disclosure will be set forth in part in the description which follows, and in part will be obvious from the description, or may be learned by practice of the present disclosure. The objects and advantages of the present disclosure will be realized and attained by means of the elements and combinations particularly pointed out in the appended claims.

It is to be understood that both the foregoing general description and the following detailed description are exemplary and explanatory only and are not restrictive of the present disclosure, as claimed.

The accompanying drawings, which are incorporated in and constitute a part of this specification, illustrate several embodiments of the present disclosure and together with the description, serve to explain the principles of the present disclosure.

DETAILED DESCRIPTION

As used herein, reference to an element by the indefinite article "a" or "an" does not exclude the possibility that more than one of the element is present, unless the context clearly requires that there is one and only one element. The indefinite article "a" or "an" thus usually means "at least one." The disclosure of numerical ranges should be understood as referring to each discrete point within the range, inclusive of endpoints, unless otherwise noted.

"Medication" includes any active ingredient, drug, supplement, or dietary supplement, including vitamins, proteins, peptides, nucleic acids, nutritional agents, and combinations thereof, and may be a medication or combination of medications selected from a variety of known classes including, but not limited to, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobactefial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, corticosteroids, cough suppressants (expectorants and mucolytics), diagnostic agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radiopharmaceuticals, sex hormones (including steroids), anti-allergic agents, stimulants and anorexics, sympathomimetics, thyroid agents, PDE IV inhibitors, NK3 inhibitors, CSBP/RK/p38 inhibitors, antipsychotics, vasodilators and xanthines. The medicine must be in a physical formulation suitable for inclusion into a separable capsule, including but not limited to a powder or granulate formulation.

Embodiments as disclosed herein are designed for administration to humans or other mammals.

It should be understood that the embodiments described herein are not limited thereto. Those having ordinary skill in the art and access to the teachings provided herein will recognize additional modifications, applications, embodiments, and substitution of equivalents that all fall with the scope of the present disclosure. Accordingly, the present disclosure is not limited by the foregoing or following descriptions.

Figure 1:
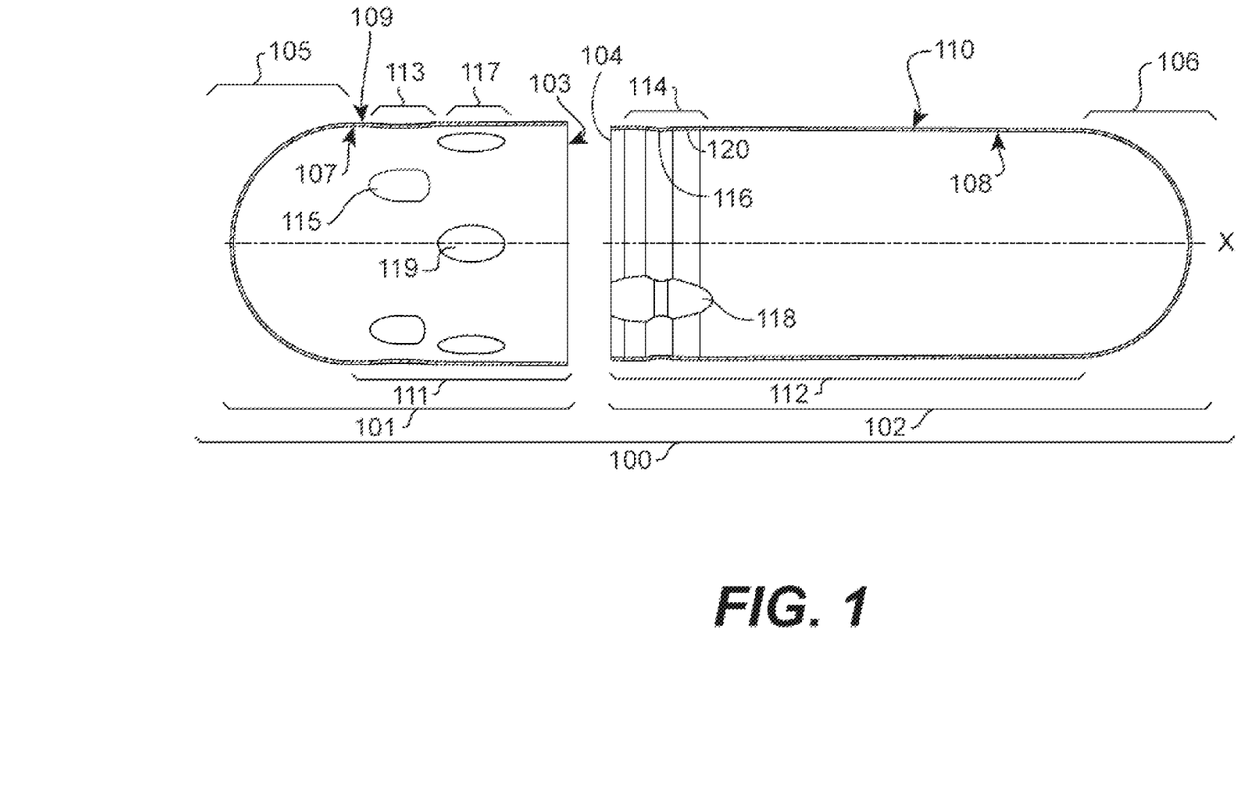
FIG. 1 is a schematic representation showing a lateral view of a two-piece hard capsule in accordance with one embodiment of the present disclosure (not to scale).

FIG. 1 shows a lateral view of a capsule 100 in accordance with one embodiment of the present disclosure. Capsule 100 comprises a first part, namely cap 101, and a second part, namely body 102. Cap 101 and body 102 each have an open end (103 and 104, respectively), a closed end (105 and 106, respectively), an inner wall (107 and 108, respectively), an outer wall (109 and 110, respectively), and a hollow cylindrically shaped portion (111 and 112, respectively). Cap 101 and body 102 are adapted such that when aligned with insertion axis X with open ends 103 and 104 facing each other, body 102 may be telescopically inserted into cap 101, thereby placing capsule 100 in a closed condition. When the capsule is in a closed condition, a cavity is formed by inner walls 107 and 108, the cavity being capable of holding a medicament or other composition. Outer wall 110 of body 102 may be configured to slide against inner wall 107 of cap 101 upon insertion of body 102 into cap 101 by defining appropriate dimensions and/or using materials of sufficient elasticity.

In the embodiment shown in FIG. 1, cap 101 further comprises a first connection unit 113 capable of engaging with a second connection unit 114 located on body 102. The connection formed by the engagement of the first connection unit 113 and the second connection unit 114 is releasable using typical human finger strength. The force needed to release or disengage the first connection unit 113 from the second connection unit 114 may range from about 30 g to about 200 grams, or from about 50 grams to about 100 grams, or from about 100 grams to about 150 grams, of force.

The first connection unit 113 may be integrally formed with the hollow cylindrically shaped portion 111 of cap 101. Thus, as shown in in FIG. 1, the first connection unit 101 may be formed by shaping inner wall 107 and/or outer wall 109. Similarly, the second connection unit 114 may be integrally formed with the hollow cylindrically shaped portion 112 of body 102, and may be formed by shaping inner wall 108 and/or outer wall 110. In this embodiment, the engagement of the first connection unit 113 and the second connection unit 114 may be provided using the telescopic joining of cap 101 and body 102—the frictional forces and/or mechanical impingements generated by the physical contact between the first connection unit and the second connection unit upon telescopic insertion of body 102 into cap 101 provide the resistance needed to prevent capsule 100 from opening spontaneously.

In certain embodiments of present disclosure, the engagement between the first connection unit 113 and the second connection unit 114 may be provided in the following manner. As shown in FIG. 1, the first connection unit 113 may comprise a plurality of protrusions 115 arrayed along the circumference of the first connection unit 113. The protrusions 115 may be arranged at regular or irregular intervals; the number of protrusions 115 may range from 2 to 10, for example 4 to 8, or 4 to 6. The protrusions 115 may have a generally elongated shape, such as an at least partially ellipsoidal or elliptical shape shown in FIG. 1. The elongated axis (axis of elongation) may be parallel to insertion axis X. The latter arrangement may bring advantages not only to the manufacturing ease of capsules and respective pins but also in reducing the locking forces to an acceptable range such that opening by hand is simplified, such without impacting locking resistance during handling and transportation to limit accidental opening. The protrusions may extend inwardly into the cavity formed by inner wall 107, and may be formed, for example, by creating indentations in the hollow cylindrically shaped portion 111 of cap 101. The second connection unit 114 may comprise a recessed ring 116 extending inwardly into the cavity formed by inner wall 108, which may be formed by creating a circumferential indention in the hollow cylindrically shaped portion 112 of body 102. The depth of recessed ring 116 may range from about 30 microns to about 85 microns. The second connection unit 114 may also comprise a tapering indentation 120 that provides a taper to recessed ring 116. Thus, when body 102 is telescopically inserted into cap 101 to a sufficient degree or depth the protrusions 115 on cap 101 may engage with the recessed ring 116 and/or tapering indentation 120 on body 102.

When the first connection unit 113 and the second connection unit 114 are engaged by telescopic insertion of body 102 into cap 101, the capsule 100 is in a locked or fully closed condition. To provide a prelocked or partially closed condition, cap 101 may comprise a third connection unit (also referred to as a prelock connection unit) 117 capable of engaging with the second connection unit 114. The third connection unit 117 may lie between the first connection unit 113 and the open end 103 of cap 101, and may be integrally formed with the hollow cylindrically shaped portion 111. The connection formed by the engagement of the third connection unit 117 and the second connection unit 114 is releasable using forces on the order of those used by typical automated capsule filling machines. The force needed to release or disengage the third connection unit 117 from the second connection unit 114 may range from about 5 grams to about 35 grams, from about 10 grams to about 30 grams, and from about 10 grams to about 25 grams, of force.

In certain embodiments of the present disclosure, the engagement between the third connection unit 117 and the second connection unit 114 may be provided in the following manner. As shown in FIG. 1, the third connection unit 117 may comprise a plurality of protrusions 119 arrayed along the circumference of the third connection unit 117. The protrusions 119 may be arranged at regular or irregular intervals; the number of protrusions 119 may range from 2 to 10, for example 4 to 8, or 4 to 6. The protrusions 119 may have a generally elongated shape, such as ellipsoidal or elliptical shape shown in FIG. 1. The elongated axis (axis of elongation) may be parallel to insertion axis X. The protrusions 119 may extend inwardly into the cavity formed by inner wall 107 and may be formed, for example, by creating indentations in the hollow cylindrically shaped portion 111 of cap 101. The second connection unit 114 may comprise a recessed ring 116 and tapering indentation 120, as discussed. Thus, when body 102 is telescopically inserted into cap 101 to sufficient degree or depth, the protrusions 119 on cap 101 may engage with the recessed ring on 116 on body 102. When the third connection unit 117 and the second connection unit 114 are engaged by telescopic insertion of body 102 into cap 101, the capsule 100 is in a prelocked or partially closed condition. The protrusions 115 may have a restriction edge generally perpendicular to the insertion axis, and the restriction edge may be configured to restrict insertion depth when inserting the body 102 into the cap 101 for engaging the prelock releasable connection.

To reduce the pressure build-up when placing the capsule 100 in a closed or prelock condition, body 102 may optionally comprise one or more vents 118. Vents 118 provide indentations that facilitate the passage of air when body 102 is telescopically inserted into cap 101. Vents 118 may be arrayed along the circumference of the hollow cylindrically shaped portion 112 of body 102, and the indentions forming vents 118 may be contiguous with the indentation forming recessed ring 116. When one or more vents are used, the protrusions 115 are arranged such that they are not aligned with any one of the vents. By the term "not aligned" it is herein intended that an axis running through the centerline of the protrusion along an insertion axis X does not run through the centerline of the vent. The arrangement has the advantage of preventing locking force variation which may otherwise result in accidental opening of the capsule during transportation and handling. Alternatively, the body 102 may be free of vents 118, this may eliminate the need for ensuring the cap is correctly oriented with the body as described above. Optionally, the body may also have a ridge at the open end 104 to facilitate engagement during joining and closing.

Figure 2A:
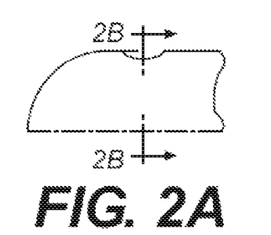
FIG. 2A, FIG. 2B, FIG. 2C, FIG. 2D, FIG. 2E, FIG. 2F, FIG. 2G, FIG. 2H, FIG. 2I, and FIG. 2J illustrate several protrusion geometries capable of use in embodiments of the present disclosure (not to scale).
Figure 2B:
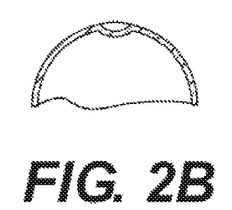
Figure 2C:
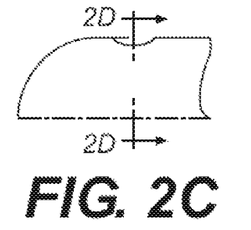
Figure 2D:
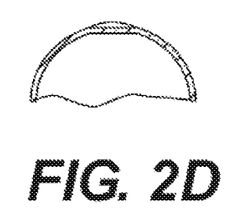
Figure 2E:
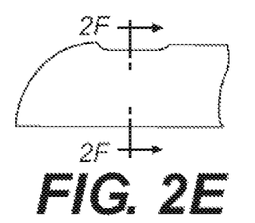
Figure 2F:
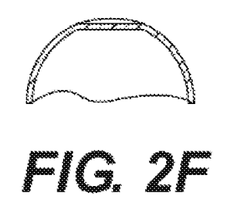
Figure 2G:
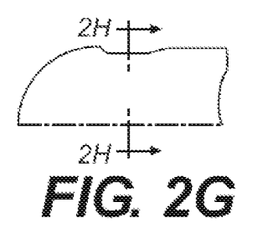
Figure 2H:
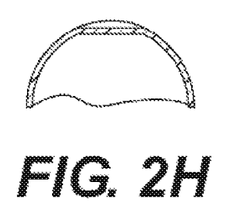
Figure 2I:
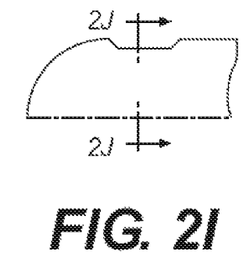
Figure 2J:
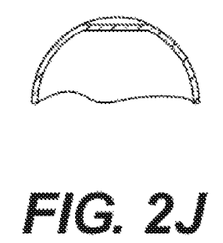

Several protrusion geometries are capable of use as protrusions 115 or protrusions 119. The individual protrusions of protrusions 115 or protrusions 119 may have the same or different geometry. Exemplary embodiments herein illustrated include: a lateral profile (FIG. 2A) and a cross-section view (FIG. 2B) of a "spherical" or "spheroid" protrusion; a lateral profile (FIG. 2C) and a cross-section view (FIG. 2D) of a "cylindrical" protrusion; a lateral profile (FIG. 2E) and a cross-section view (FIG. 2F) of a cylindrical protrusion with an elongated flat region; a lateral profile (FIG. 2G) and a cross-section view (FIG. 2H) of a cylindrical protrusion with an elongated flat region with a single angled end; and a lateral profile (FIG. 2I) and a cross-section view (FIG. 2J) of a cylindrical protrusion with an elongated flat region with two angled ends.

Spherical or spheroidal protrusions and cylindrical protrusions may be further described in terms of a radius R and depth D. A spherical, spheroidal, or cylindrical protrusion having radius R has a radius of curvature corresponding a sphere or cylinder having radius of the same length as radius R. For spheroidal protrusions, including the ellipsoidal or elliptical protrusions such those shown in FIG. 1, an additional parameter such eccentricity may also further describe the protrusion. Depth D is a measure of the degree of inward displacement from e.g. inner wall 107.

Figure 3:
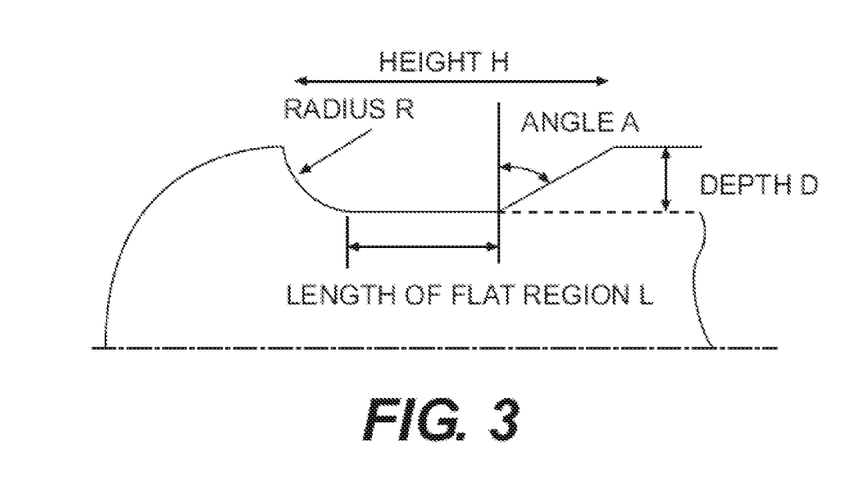
FIG. 3 illustrates various design parameters of protrusions capable of use in embodiments of the present disclosure (not to scale).

Variation in protrusion geometry may also be introduced using a flat region and using different shapes for the protrusion ends, in particular partially spherical, cylindrical or angled ends. Thus, as shown in FIG. 3, a protrusion may be defined using radius R corresponding to the radius curvature of a partially spherical or cylindrical end, length L of the flat region, angle A corresponding the angle formed by a flat end, and height H of the protrusion. Radius R may range from about 1.5 millimeters to about 10 millimeters, e.g. from about 5 millimeters to about 9 millimeters; length L may range from about 0 millimeters to about 1 millimeter, e.g. from about 0 millimeters to about 0.5 millimeters; angle A may range from about 0 degrees to about 90 degrees, e.g. from about 30 degrees to about 60 degrees; depth D may range from about 40 microns to about 200 microns, e.g. from about 100 microns to about 180 microns; and height H may range from about 0.8 millimeters to about 4 millimeters, e.g. about 2 millimeters to about 3 millimeters. An exemplary embodiment of a protrusion in accordance with the present disclosure may comprise a partially spherical or cylindrical end and an angled end, wherein the angled end is between the partially spherical or cylindrical end and the open end of a capsule part, and the protrusion has radius R of about 6.2 millimeters, length L of about 0.1 millimeters, angle A of about 45 millimeters, depth D of about 160 microns, and height H of about 2.3 millimeters.

Capsules in accordance with the present disclosure can be produced by methods commonly applied for the production of telescope-type capsules, e.g., by means of dip molding processes with metal pins whose profiles have been made on the basis of the optimized parameters. Production by means of injection molding is possible. While the production of telescope-type capsules for pharmaceutical or comparable applications which make use of smaller capsule dip molding is currently preferred, it may be advantageous for the production of larger containers made of other materials to use injection molding or other suitable methods.

Capsules in accordance by the present disclosure may be produced from various materials. For the production of smaller telescope-type capsules, the outer skin of which is to disintegrate, e.g., in the digestive tract or after they have been introduced into the mouth, gelatin, alginates, cellulose ester, methyl cellulose, cellulose ether ester, acrylic resins, or substances having similar suitable properties can be used. Specifically, when injection molding methods are applied for the production of the capsules, use can be made also of starch. Various additives can be added, such as, e.g., glycerine, propylene glycol, monoacetin, diacetin and triacetin, glycol diacetate, polyols, such as sugar or polyvinyl alcohol, gelatin, hydrophilic polymers, vegetable proteins, water-soluble polysaccharides, such as, e.g., carrageenan or guar gum, blood proteins, egg proteins, acrylated proteins, and others. Equally, dyestuffs and bactericides may be added to telescope-type capsules. Other materials can be used as well, such as, e.g., thermoplastic polymers.

The present disclosure may also be applied in capsules of all sizes, including standard and elongated sizes, such as e.g., Size No. 000, No. 00 No. 0, No. 1, No. 2, No. 3, No. 4, and No. 5, for example, with diameters from about 4 millimeters to about 14 millimeters, and lengths from about 10 millimeters to about 30 millimeters. Certain embodiments of the present disclosure are capsules of standard or elongated Size No. 00 and 0. The capsules may range in diameter from about 4 millimeters to about 14 millimeters. The length of the capsules may range from about 10 millimeters to about 30 millimeters, particularly from about 11 to about 27 millimeters.

Figure 4:
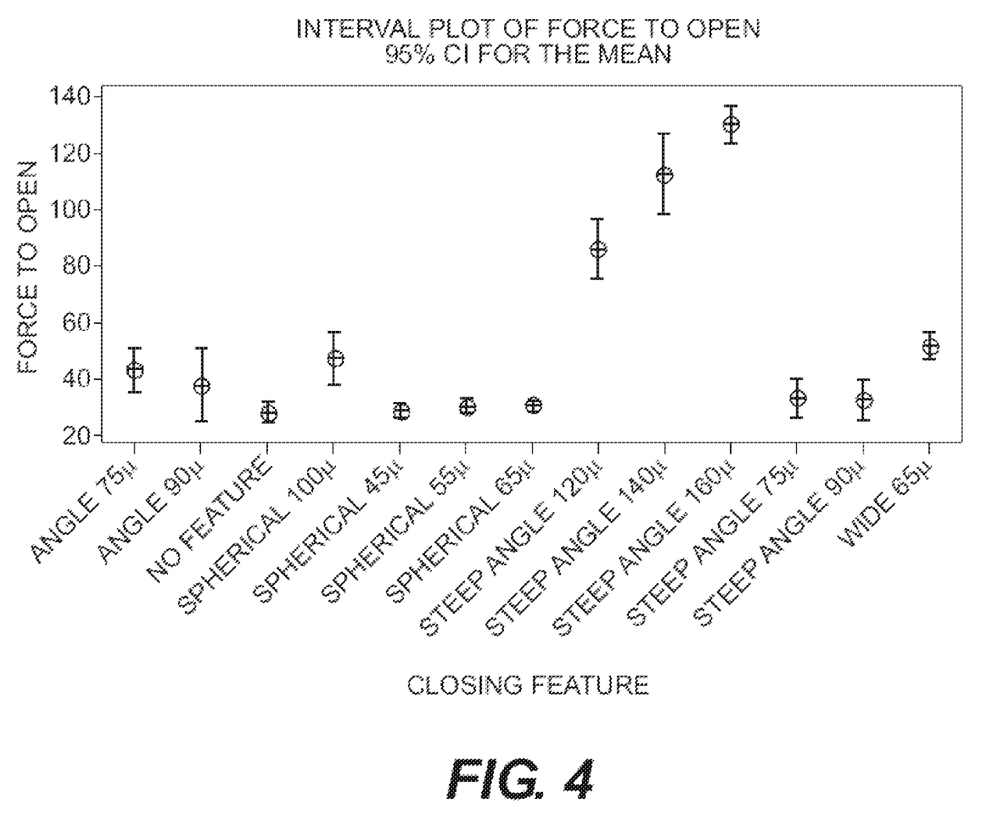
FIG. 4 depicts an interval plot of force in grams to open various types of capsules.
Figure 5:
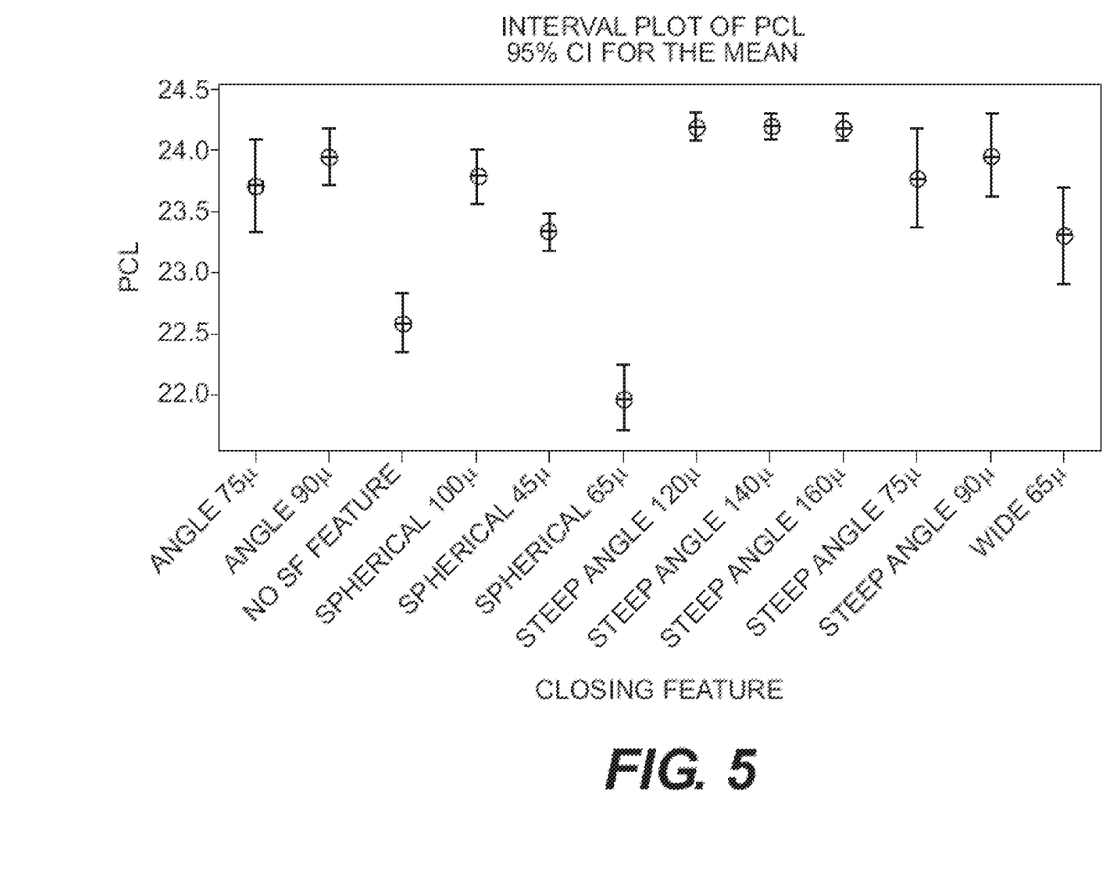
FIG. 5 depicts an interval plot of pre-closed length (PCL) in millimeters of various types of capsules.

Table 1 provides the parameters of various closing features tested for closing force in FIGS. 4 and 5. Force to open is reported in grams of force, and PCL in mm. The separable capsules tested were all standard size #0 gelatin capsules formed by a dip molding process, with a closed length of 21.7 millimeters and a pre-closed length (PCL) of 24.2 millimeters. The external body diameter was 7.34 millimeters, with a wall thickness of about 105 micrometers. The depth of the locking ring was 55 micrometers. The tested capsules also had a ridge at the body edge to facilitate engagement.

Testing was performed at Capsugel, using a device incorporating a commercially available Shimpo digital force gauge. The body of the capsule was fixed with a needle in the holder, and the force required to remove the cap was recorded. FIGS. 4 and 5 show the mean of each test with error bars showing the 95% confidence interval.

Table 2 illustrates the average % fill of pockets in a printing machine belt. The higher the % fill, the less empty pockets, resulting in higher throughput of printed capsules. Numbers have been averaged over a printing trial of 10,000 capsules. % fill are shown for capsules having (i) cap locking feature (i.e. plurality of first coupling elements) but free of body locking feature (i.e. second coupling element) or (ii) a cap locking feature (i.e. first coupling elements) and body locking feature (i.e. second coupling element).

TABLE 1

| Type | R (mm) | D (μ) | a (°) | L (mm) | Remark |
| --- | --- | --- | --- | --- | --- |
| No feature | | NA | | | |
| Spherical 45μ | 8.65 | 45 | | NA | |
| Spherical 55μ | 8.65 | 55 | | NA | |
| Spherical 65μ | 8.65 | 65 | | NA | |
| Spherical 100μ | 8.65 | 100 | | NA | |
| Wide 65μ | 8.65 | 65 | | NA | Shape adapted to increase indent's width around part's circumference |
| Angle 75μ | 6.2 | 75 | 75 | 0.5 | |
| Angle 90μ | 6.2 | 90 | 75 | 0.5 | |
| Steep angle 75μ | 6.2 | 75 | 45 | 0.7 | |
| Steep angle 90μ | 6.2 | 90 | 45 | 0.7 | |
| Steep angle 120μ | 6.2 | 120 | 45 | 0.1 | |
| Steep angle 140μ | 6.2 | 140 | 45 | 0.1 | |
| Steep angle 160μ | 6.2 | 160 | 45 | 0.1 | |

TABLE 2

| Type | % fill rate |
| --- | --- |
| Cap locking feature + No Body locking feature | <75% |

TABLE 2-continued

| Type | % fill rate |
|---|---|
| Plurality of coupling elements on cap as locking feature + Body locking feature (recess) | >98% |

Other embodiments of the present disclosure will be apparent to those skilled in the art from consideration of the specification and practice of the present disclosure. It is intended that the specification and examples be considered as exemplary only, with a true scope and spirit of the present disclosure being indicated by the following claims.

We claim:

1. A two-piece releasable hard capsule comprising:
a first part having an open end, a closed end, insertion axis, and a first connection unit having a lock area comprising a plurality of first coupling elements;
a second part having a second connection unit, wherein the second connection unit has an engagement area comprising a second coupling element, the engagement area being configured to engage with the lock area when the second part is fully inserted in the first part in a fully closed position, forming a locked connection, wherein the locked connection is releasable by a finger force being a first force of from about 30 grams to about 200 grams, wherein the plurality of first coupling elements comprise protrusions elongate in shape comprising an elongated axis running parallel to an insertion axis and comprising a restriction edge perpendicular to the insertion axis.

2. A capsule according to claim 1, wherein the first force is from about 50 grams to about 150 grams.

3. A capsule according to claim 1, wherein the second coupling element comprises an indentation having a recessed ring, wherein the recessed ring has an asymmetric cross-section along the insertion axis.

4. A capsule according to claim 1, wherein the first coupling elements have a depth of about 50 microns to about 200 microns.

5. A capsule according to claim 1, wherein the first connection unit further comprises a prelock area comprising a plurality of third coupling elements, and wherein the engagement area is configured to engage with the prelock area when the second part is partially inserted in the first part to form a prelock releasable connection, releasable by a second force.

6. A capsule according to claim 1, wherein the restriction edge is configured to restrict insertion depth when inserting the second part into the first part for engaging a prelock releasable connection.

7. A two-piece releasable hard capsule comprising:
a first part having an open end, a closed end, insertion axis, and a first connection unit comprising:
an inner wall defining a first cavity;
a prelock area; and
a lock area, wherein at least part of the lock area is located between the prelock area and the dosed end; and
a second part having a second connection unit comprising:
an outer wall insertable into the first cavity along the insertion axis through the open end; and
an engagement area configured to engage with the prelock area when the outer wall is partially inserted in the first cavity to form a first releasable connection between the first part and the second part, and
wherein the engagement area is configured to engage with the lock area when the outer wall is fully inserted in the first cavity in a fully closed position forming a locked connection, wherein the locked connection is a second releasable connection between the first part and the second part, wherein the first releasable connection requires a first force to release and the second releasable connection requires a second force to release, wherein the ratio of the first force to second force is from about 0.15 to about 0.35, wherein the prelock area comprises a plurality of first coupling elements, the lock area comprises a plurality of second coupling elements, and the engagement area comprises a third coupling element,
wherein at least one of the second coupling elements has a restriction edge perpendicular to the insertion axis, wherein the restriction edge is configured to restrict insertion depth when inserting the second part into the first part and engaging the first releasable connection, and wherein at least one of the plurality of first coupling elements and the plurality of second coupling elements comprises a protrusion having an elongated shape comprising an elongated axis running parallel to an insertion axis and comprising a restriction edge perpendicular to the insertion axis.

8. A capsule according to claim 5, wherein the second force is from about 10 grams to about 30 grams.

9. A capsule according to claim 5, wherein the second force is from about 10 grams to about 25 grams.

10. A capsule according to claim 5, wherein the plurality of first coupling elements of the first connection unit are located farther from the open end than the plurality third coupling elements, wherein a longitudinal axes of the plurality of first coupling elements and the plurality of third coupling elements is parallel to the insertion axis.

11. A capsule according to claim 7, wherein the third coupling element comprises an indentation having a recessed ring.

12. A method of using a two-piece releasable hard capsule according to claim 1 for administering medication, comprising:
providing a two-piece releasable hard capsule at least partially filled with a medication;
applying a finger force to the two-piece releasable hard capsule to disengage a releasable connection and separate the two-pieces of the capsule;
removing the medication from the two-pieces of the capsule and combining the medication with at least one of a food or a drink to produce a mixture; and
providing the mixture to a patient for consumption.

13. A capsule according to claim 1, wherein the area of contact between the lock area and the engagement area is from about 20% to about 50% of the total surface area of the engagement area.

14. A capsule according to claim 1, wherein the first coupling elements have a depth of about 75 microns to about 160 microns.

15. A capsule according to claim 1, wherein the finger force is between about 100 grams and about 150 grams.

16. A capsule according to claim 1, wherein the finger force is between about 50 grams and about 150 grams.

17. A capsule according to claim 1, wherein the first connection unit further comprises a prelock area comprising a plurality of third coupling elements, and wherein the engagement area is configured to engage with the prelock area when the second part is partially inserted in the first part to form a prelock releasable connection and wherein the plurality of third coupling elements have a depth of about 40 microns to about 90 microns.

18. A capsule according to claim 17, wherein the prelock release connection is released by a force of about 10 grams to about 30 grams.

19. A capsule according to claim 11, wherein the recessed ring has an asymmetric cross-section along the insertion axis.

20. The method of claim 12, wherein the two-piece releasable hard capsule is configured to form a prelock connection that is released prior to filling of the capsule, and following filling of the capsule the two pieces are reattached and the releasable connection is formed.

* * * * *

UNITED STATES PATENT AND TRADEMARK OFFICE
CERTIFICATE OF CORRECTION

PATENT NO. : 9,775,813 B2
APPLICATION NO. : 14/774119
DATED : October 3, 2017
INVENTOR(S) : Hilde Buydts et al.

It is certified that error appears in the above-identified patent and that said Letters Patent is hereby corrected as shown below:

In the Specification

Column 3, Line 55, "none of capsules" should read --none of the capsules--.

Column 6, Line 40, "all fall with the" should read --all fall within the--.

Column 7, Line 38, "such without" should read --such as without--.

Column 9, Line 21, "corresponding the angle" should read --corresponding to the angle--.

In the Claims

Column 12, Line 32, "plurality third" should read --plurality of third--.

Signed and Sealed this
Sixth Day of April, 2021

Drew Hirshfeld
*Performing the Functions and Duties of the
Under Secretary of Commerce for Intellectual Property and
Director of the United States Patent and Trademark Office*